United States Patent
Kang et al.

(10) Patent No.: US 8,318,962 B2
(45) Date of Patent: Nov. 27, 2012

(54) PROCESS FOR RECOVERING STEROLS FROM A CRUDE SOURCE CONTAINING STEROL ESTERS

(75) Inventors: Sang I. Kang, Bourbonnais, IL (US); Joseph J. Falatek, Kankakee, IL (US); Brian P. Thiesen, Bourbonnais, IL (US); Kenneth R. Bicknell, Bourbonnais, IL (US)

(73) Assignee: Cognis IP Management GmbH, Duesseldorf (DE)

( * ) Notice: Subject to any disclaimer, the term of this patent is extended or adjusted under 35 U.S.C. 154(b) by 1286 days.

(21) Appl. No.: 11/961,463

(22) Filed: Dec. 20, 2007

(65) Prior Publication Data

US 2008/0161586 A1 Jul. 3, 2008

Related U.S. Application Data

(60) Provisional application No. 60/882,611, filed on Dec. 29, 2006.

(51) Int. Cl.
*C07J 9/00* (2006.01)
(52) U.S. Cl. .................................................... 552/545
(58) Field of Classification Search ................... 552/545
See application file for complete search history.

(56) References Cited

U.S. PATENT DOCUMENTS

| | | | | |
|---|---|---|---|---|
| 2,866,797 A | * | 12/1958 | Berry et al. | 552/545 |
| 3,691,211 A | * | 9/1972 | Julian | 552/545 |
| 4,298,539 A | | 11/1981 | Koskenniska | |
| 4,524,024 A | | 6/1985 | Hughes | |
| 6,057,462 A | | 5/2000 | Robinson et al. | |
| 6,107,456 A | | 8/2000 | Huibers et al. | |
| 6,231,915 B1 | * | 5/2001 | van Amerongen et al. | 426/611 |
| 6,465,665 B1 | * | 10/2002 | Schersl | 552/545 |
| 2005/0033068 A1 | | 2/2005 | Hamunen et al. | |
| 2006/0035009 A1 | | 2/2006 | Gaonkar et al. | |

FOREIGN PATENT DOCUMENTS
EP 1 250 350 B1 4/2006
* cited by examiner

*Primary Examiner* — Barbara P Badio
(74) *Attorney, Agent, or Firm* — Diehl Servilla LLC

(57) ABSTRACT

A process of obtaining sterols suitable for human consumption from a crude wood pulping source containing sterol esters is disclosed. The sterols are obtained at high yield and purity. In particular, a process of obtaining sterols at high yield and purity from tall oil pitch (TOP) is disclosed. The sterols obtained can be esterified to sterol esters for use in dietary supplements and as additives for food and beverage products.

11 Claims, No Drawings

PROCESS FOR RECOVERING STEROLS FROM A CRUDE SOURCE CONTAINING STEROL ESTERS

CROSS-REFERENCE TO RELATED APPLICATIONS

This application claims priority under 35 U.S.C. Section 119 of U.S. Provisional Application No. 60/882,611 filed Dec. 29, 2006, the contents of which are incorporated herein by reference in its entirety.

BACKGROUND OF THE INVENTION

Naturally occurring phytosterols have generated strong interest in the functional food industry as the plant sterols have been proven to lower the levels of serum low-density lipoprotein (LDL), the so-called bad cholesterol in humans. Phytosterols are plant compounds with chemical structures similar to that of cholesterol. This structural and functional similarity of phytosterols can actually block food-based cholesterol from being absorbed into the bloodstream. The result is that both phytosterols and dietary cholesterol end up excreted in waste matter.

Tall-oil-pitch (TOP) is an undistilled residue from the distillation of crude tall oil (CTO), which is a dark brown mixture of fatty acids, rosin, and neutrals including phytosterols, liberated by the acidulation of soap skimmings from the alkali (sulfate) process, derived from wood pulping processes, which are primarily used in making paper. Typical TOP is known to have about 15% free and bound sterols, about 40% free and bound fatty and rosin acids, about 10% bound wax alcohols ($C_{16-30}$ alcohols), about 25% heavy molecules, and about 10% other compounds of terpenoids, steroids, and unknowns. A major component of the neutral fraction, concentrated in the TOP of the CTO, is a class of compounds known as phytosterols, including β-sitosterol as the major sterol component.

There has been a great deal of interest and effort in recovering the phytosterols and their derivatives of fatty acids and other biologically significant molecules, which are particularly useful as dietary supplements and as food additives, in order to reduce cholesterol levels in humans, thus reducing the risk of heart disease, according to current clinical studies.

Therefore, the interest and value of recovering phytosterols from TOP sources has increased, and the resolution of all of the problems associated with recovering phytosterol from TOP have become of great interest. It is most desirable that a viable commercial process achieves a high percent recovery of sterols (greater than 70% recovery is preferable), while desirably achieving sterol purity of at least 98%.

During recovery of high purity phytosterols, a class of natural molecules of fatty alcohols also known as wax alcohols and policosanol, present in TOP, was found to co-crystallize with phytosterols. Policosanol is a natural mixture of fatty alcohols ubiquitous in plant waxes. The TOP feed that we processed contains common aliphatic alcohols in which three significant policosanols are present, namely, 1-dodecosanol, 1-tetracosanol, and 1-hexacosanol.

As described hereinafter, the invention addresses this problem and achieves the desired yield and purity of phytosterols from TOP prevailing over fatty alcohols and other undesirable impurities, and describes making corresponding phytosterol esters using different acylating reagents.

U.S. Pat. No. 6,465,665 discloses a process of obtaining, inter alia, sterols from TOP in which the process achieves sterol purities of 95-96%. See Examples 3 and 4. This patent describes a continuous process for the recovery of sterols from mixtures of neutral matter obtained from crude tall oil (CTO) black liquor soap skimmings or tall oil pitch, comprising the steps of a series of distillations using a rectifying column, condenser and thin film reboiler so as to form a first to fourth fractions comprising long chain aliphatic alcohols, sterols concentrate and esters, sterols concentrate, and sterol esters depending on the distillation stages. Then the third fraction was recrystallized from a mixture of a hydrocarbon solvent, short chain aliphatic alcohol, and water. The residue from the mother liquor was recycled as the mixture of neutral matter of very first feed.

EP 1250350B1 describes a composite crystalline structure comprising a phytosterol or a derivative thereof and a phytostanol or a derivative thereof prepared by dissolving a phytosterol or esterified derivative thereof purified from its source and a phytostanol or esterified derivative thereof purified from its source in a solvent at an ambient temperature or temperature above ambient but lower than the boiling point of the solvent, cooling the solvent to allow crystal formation; and filtering and washing the crystals so formed; wherein the structure has a single composite endotherm as determined using differential scanning calorimetry.

It remains desirable to provide a process that achieves even higher purity levels of sterols recovered from TOP. As discussed hereinafter, the process of the present invention provides such desirable higher purity levels of sterols.

BRIEF SUMMARY OF THE INVENTION

The invention provides a process for recovering sterols from a crude source containing free sterols and their esters, which process comprises;
  (a) saponifying the crude source containing sterol esters to form free sterols;
  (b) extracting the free sterols of (a) with an organic solvent to yield an extract of a crude sterol concentrate containing from about 70 to 80% sterols by weight and fatty alcohols;
  (c) removing the fatty alcohols present in the extract to an amount of 7% or less fatty alcohols remaining in the extract;
  (d) crystallizing the extract of (c) with a solvent mixture of a $C_1$-$C_{10}$ hydrocarbon solvent present in an amount of about 60 to 99% by weight of the mixture, a $C_1$-$C_{10}$ lower alkanol present in an amount of about 0.1 to 20% by weight of the mixture, and water present in an amount of about 0.1 to 20% by weight of the mixture, to form crystallized sterols; and
  (e) recovering the crystallized sterols of (d) at a purity of at least or greater than 98%.

Another embodiment of the invention is directed to esterifying the crystallized sterols obtained by the process of the invention to sterol esters with an acylating agent to yield sterol esters of purity greater than about 98%.

Another aspect of the invention is that the crude sterol concentrate obtained by the extraction step of the present invention can be further treated by crystallization or distillation and crystallization.

In one embodiment of the invention, the crude source containing sterol esters, from which the desired sterols are obtained, is TOP, which is the undistilled residue obtained from the distillation process of CTO.

By way of the invention, sterols, particularly β-sitosterol, are obtained at yields of or greater than 70% and of at least 98%, preferably greater than 98.5% purity in crystalline form. The sterols obtained by way of the present invention can be esterified to sterol esters for use as dietary supplements and as additives to food and beverage products.

DETAILED DESCRIPTION OF THE INVENTION

The term "high purity" as used herein shall be understood to encompass a sterol purity achieved by way of the process of the present invention of at least 98% and preferably greater than 98.5%.

The TOP fraction containing sterol esters is subjected to saponification, which saponification hydrolyzes the sterol esters and other sterol derivatives to sterols and sodium salts of fatty acids and rosin acids. The saponified fraction can then be extracted with an organic solvent so as to form aqueous and organic phases. The solvent extraction can be carried out one or more times, as desired, to maximize sterol recovery. The extraction can be carried out at temperatures of from about 50° to 80° C.

A suitable solvent for the extraction can be selected from water-immiscible organic solvents such as hexane, heptane, ethyl acetate, ethylene dichloride (EDC), and mixtures of thereof. The preferred solvent is EDC.

The resultant organic phases, containing the sterols, can then be combined and concentrated, so as to obtain a crude sterol concentrate (TOP-SC) of about 25 to 40% sterol concentration by weight, typically about 35%, with AV 3.6 and SV 17.7.

In one embodiment of the invention, the TOP-SC can undergo two separate crystallization steps.

The TOP-SC can undergo a first crystallization with a solvent, preferably ethylene dichloride, to achieve a sterol fraction of about 70 to 80% sterol purity.

The crystallized sterols obtained from the TOP-SC contain about 5-15% fatty alcohols, typically about 10%, which can then be further treated by either simple or fractional distillation to remove the mixture of fatty alcohols as light distillates, resulting in a crude sterol residue with 85-95% sterol concentration. Preferably, the fatty alcohols are removed to an amount of 7% or less remaining in the sterol residue.

The residue sterols, to achieve a purity of at least or greater than 98%, can be crystallized with a solvent mixture of a $C_1$-$C_{10}$ hydrocarbon solvent, a $C_1$-$C_{10}$ lower alkanol, and water at a temperature of from about 50° C. to 70° C. Suitable weight ratios of the components of the solvent mixture for crystallization of the sterols can range from about 60 to 99.8% by weight of the hydrocarbon, about 0.1 to 20% by weight of the lower alkanol, and about 0.1 to 20% by weight of water.

Particularly suitable ratios by weight of the solvent mixture can be, for example, about 80 to 98% hydrocarbon solvent, about 1 to 10% $C_1$ to $C_6$ alkanol, and about 1 to 10% water.

The hydrocarbon solvent can be a straight- or branched-chain hydrocarbon of from 1 to 10 carbon atoms. Heptane, including a mixture of linear and branched $C_7H_{16}$ heptanes, is particularly suitable for use in the invention.

The lower alkanol of the solvent mixture can be a $C_1$-$C_{10}$ alkanol, preferably methanol.

Thus, particularly suitable solvents and their ratios by weight of the solvent mixture for use in the invention for crystallization of the sterols to a purity of at least 98% can be comprised of about 80 to 99% heptane, about 0.5 to 10% methanol, and about 0.5 to 10% water.

Other suitable non-limiting examples of solvents for use in the invention can include n-propanol, isopropanol, acetone, MEK, ethyl acetate, cyclohexane, ethanol, and mixtures with water thereof.

The residue sterols after reduction of the light boilers are dissolved in heptanes at elevated temperature (55-75° C.).

Upon forming a homogeneous sterol solution, the aqueous methanol (0.1-10% by weight) is added with agitation to precipitate sterols in the mixed solvents. The hot solution is cooled to a temperature of about 20° to 25° C., with stirring, to promote crystallization of the sterols.

The amount of solvent to sterols can range from about 400 to 1,200% of the amount of sterols by weight, preferably from about 500 to 700% by weight.

The sterol crystals can be isolated by filtering and washing with, for example, heptanes. Washing of the sterol crystals can also be carried out with a mixture of heptanes/methanol/water.

Another embodiment of the invention is directed to distillation of the TOP-SC fraction to obtain an intermediate sterol concentrate (TOP-SCD) of about 40 to 70% sterols by weight, which distillation removes heavy boilers, which are considered to be oligomerized fatty acids and/or rosin acids and waxy compounds.

The crude sterols can be distilled in a two-stage process. In the first step, a fractionating column and a wiped film evaporator as a reboiler can be utilized. A low boiling fraction (up to 20% of the feed) can be removed by vacuum fractionation. In a second step, the residue of the first step can be distilled in a short path evaporator under vacuum of <1 mbar to form a purified sterol fraction to be crystallized. The distillate fraction is >90% of the feed.

The TOP-SCD distilled fraction obtained as described above can then be treated to crystallize the sterols for recovering at a high yield and high purity with a solvent mixture of hydrocarbon, lower alkanol, and water, as described above.

By way of the present invention, sterols, particularly β-sitosterol, can be obtained in yields of at least 70% and purity of at least 98%, preferably greater than 98.5% from a crude source containing sterol esters. In particular, the sterols of the above described yield and purity can be obtained from the TOP fraction of CTO obtained from wood pulping processes.

The sterols obtained by way of the present invention from TOP can then be converted to corresponding phytosterol esters using acylating reagents such as fatty acids, fatty acid anhydrides, and fatty acid halides, which acylating agents are well-known in the art and which can be selected according to the desired sterol ester. The corresponding sterol esters are suitable for use in dietary supplements and as additives to food and beverage products.

PREFERRED EMBODIMENT OF THE PROCESS OF THE INVENTION

The present invention provides for the recovery of TOP phytosterols, typically from sources in which the sterols are mostly bound in a mixture of fatty and rosin compounds. The sterol esters and other functional derivatives can be saponified in a strong alkaline aqueous methanol, rendering pH of >12 at the end of saponification. The neutrals, including sterols present in the resulting soap solution, can then be extracted with EDC, and its concentrate crystallized to provide crude sterols with a purity of 70-80% sterols. The crude sterols can then be distilled in a two-stage process to obtain a heart cut. In the first step, comprising a fractionating column and a wiped film evaporator as reboiler, a low boiling fraction (up to 20% of the feed) can be removed by vacuum fractionation. In a second step, the residue of the first step can be distilled in a short path evaporator under vacuum of <1 mbar to form a purified sterol fraction to be crystallized. The distillate fraction is >90% of the feed. The distillate (or the G100) can then be dissolved in an alkane, preferably a mixture of hexanes and heptanes, at 60-70° C. and mixed with aqueous methanol in which the amount of methanol and water ranges from 0-3% of the amount of the alkane, preferably 1.5% methanol and 1.5% water. The mixture can then be chilled to about 20-30° C. To improve purity and color, the filter cake can be washed with a suitable amount of alkane/methanol/Water mixture, followed by drying the sterol cakes. The sterol cakes are of >98.5% sterol purity as the end product.

The following examples are illustrative of the present invention and should not be construed in any manner as limiting the scope of the present invention.

EXAMPLE 1

TOP Sterol Recovery

A. TOP Sterol Concentrate (TOP-SC): Tall oil pitch (326.7 g; 94.7 SV, 34.8 AV and 14.27% sterols by wt %) was saponified with 50% caustic (67.9 g) in 50% aqueous methanol at 85° C. for 1.5-h with agitation in a 2-l jacketed reactor. Into the mixture was added soft water (330 g), and the resulting mixture extracted with ethylene dichloride (EDC, 900 mL×4) at 60-65° C. Combined EDC layers was transferred into a round-bottomed flask and concentrated in vacuo to obtain crude sterols (116.8 g). GC analysis showed the crude sterol concentrate to be 33.9% with the following sterol profile of brassicasterol, 0.27; campesterol, 2.59; ergostanol, 0.52; stigmasterol, 0.38; β-sitosterol, 26.43; stigmastanol, 3.70(%). Major wax alcohols as impurities are 0.97% C22-OH, 6.27% C24-OH, and 1.80% C26-OH.

B. Crystallization of Sterol Concentrate: Sterol concentrate (114.8 g) was dissolved in EDC (201.8 g) and heated to 80° C. for complete dissolution. The mixture was then treated with aqueous methanol (4.84 g). Resulting solution was kept in a refrigerator for a few hours to overnight. The sterol solids were filtered on a Büchner funnel, and washed carefully with cold EDC at 0-5° C. Wet sterol cake was placed in a vacuum oven and dried to give 41.87 g of crude TOP sterols (GENEROL® 400), ranging 70-80% sterol purity with AV 1.3 and SV 3.3. Wax alcohols of C22, C24 and $C_{26}$ alcohols were present at the levels of 0.77%, 6.18% and 2.43%; respectively.

C. Crystallization of G400: Heptanes (100.0 g) were charged to a double jacketed lab crystallizer. Crude TOP sterols of 70-90% purity were added in such a way to make 10-20% solution, preferably 12%. The temperature was raised to 60-65° C. with agitation. Once the sterols were dissolved, the solution was held at the same temperature for 10 mins. to ensure the homogeneity of the sterol solution in heptanes. Then a mixture of MeOH and water (1/1, w/w) in the range of 0.1-5.0% of the total solvents of heptanes/MeOH/water was added at 60-65° C. A preferred ratio of heptanes/methanol/water is (92-99)/(0.5-4.0)/(0.5-4.0) by weight %. Resulting mixture was cooled to 25° C. at a rate of 2° C./min, and the sterol slurry held for 5 mins. at the same temperature. The sterol slurry was filtered under vacuum (500-700 mmHg), and the cake rinsed with heptanes. The cake was transferred in a crystal dish to dry at 60-70° C. (20-40 mbar) for 5-10 hours. GC analysis of dried sterols showed 86.7% purity (6.3%, campesterol; 1.0%, ergostanol; 1.0%, stigmasterol; 69.5%, β-sitosterol; 9.0%, stigmastanol) with near 10% wax alcohols as the major class of impurities.

D. Distillation of G400: To reduce the wax alcohols, GENEROL® 400 was distilled to obtain a heart cut by removing a fore cut and a residue cut. Table 1 below shows four heart cuts of G400 ($2^{nd}$ column) with different forecut and residue cuts and results (last column) of their crystallization from the aforementioned heptanes/methanol/water system. The heart cut of Distill IV gave the highest sterol purity, suggesting that the deep fore cut (23.5%) reduced the level of wax alcohols.

TABLE 1

Heart Cuts of GENEROL ® 400 Distillations

| | g/100 gm Feed | | | % Sterols | | |
|---|---|---|---|---|---|---|
| | Fore Cut | Heart Cut | Residue Cut | Fore Cut | Heart Cut | Residue Cut |
| Distill I | 11.36 | 78.9 | 9.75 | 58.72% | 87.31% | 32.13% |
| Distill II | 12.6 | 76.83 | 10.57 | 59.64% | 89.07% | 43.26% |
| Distill III | 15.01 | 74.65 | 10.33 | 61.16% | 85.77% | 33.05% |
| Distill IV | 23.49 | 69.34 | 7.16 | 73.11% | 88.86% | 34.94% |

| | gm Sterols/100 g feed | | | | Purity |
|---|---|---|---|---|---|
| | Distillate Cut | Heart Cut | Residue Cut | Total | GC Method |
| Distill I | 6.67 | 68.89 | 3.13 | 78.69 | 97.71% |
| Distill II | 7.51 | 68.43 | 4.57 | 80.52 | 97.65% |
| Distill III | 9.18 | 64.03 | 3.41 | 76.62 | 98.68% |
| Distill IV | 17.17 | 61.62 | 2.50 | 81.29 | 99.32% |

E. Effect of Wax Alcohol Concentration on Finished Sterol Purity: 1-Docosanol n-$C_{22}H_{45}$OH (Aldrich), selected as the model compound for total wax alcohols of $C_{18-30}$—OH, was spiked with a pure sterol product (>99%) in an amount varying from 6-10% as shown in Table 2. Effect of the concentration of 1-docosanol present in the feed on the purity of the crystallized sterols is summarized in Table 2, which demonstrates that less than or equal to 7% of the fatty alcohol provided satisfactory results with high purity sterols (>98.5%) and less than 0.2% fatty alcohols. The last column in the Table 2 indicates the ending temperature of the crystallization as described in Example 1C, suggesting that the final crystallization temperature influenced the sterol purity of finished product. It was found that either keeping the crystallization solution for a prolonged period or at lower temperature caused the fatty alcohols to precipitate out, lowering the overall sterol purity.

TABLE 2

Wax Alcohol Concentration Effect on Sterol Purity

| | Crystallized Product | | Final Temp |
|---|---|---|---|
| % 1-Docosanol | Sterol Purities | 1-Docosanol | ° C. |
| 10.0 | 94.81 | 4.16 | 27 |
| 8.0 | 98.05 | 0.96 | 27 |
| 7.0 | 98.99 | 0.19 | 30 |
| 6.0 | 98.99 | 0.1 | 27 |

Based on the results in Table 2, the current crystallization solvent system of heptanes/methanol/water, a feed with <7% fatty alcohols would be suitable for crystallization to make the high sterol purity.

The typical composition of the crystalline sterols produced by current process has the following sterol profile:

| Crystallized Finished Product (GENEROL ® 867F) | | |
|---|---|---|
| Total Sterols | area-% | min 99.0 |
| Cholesterol | area-% | 0.0-1.0 |
| Brassicasterol | area-% | 0.0-2.0 |
| Campesterol | area-% | 0.0-15.0 |
| Campestanol | area-% | 0.0-5.0 |
| Stigmasterol | area-% | 0.0-2.0 |
| β-Sitosterol | area-% | 60.0-85.0 |
| β-Sitostanol | area-% | 0.0-15.0 |
| Δ5-Avenasterol | area-% | 0.0-2.0 |
| other sterols | area-% | 0.0-5.0 |

"Other sterols" are the sum of cholestanol, 24-methylenecholesterol, Δ7-campesterol, Δ5,23-stigmastadienol, clerosterol, and Δ4,24-stigmasatdienol.

F. Sterol Esters: Three acylating agents a-c are to be used in the esterification of sterols;

a: oleic acid (or fatty acids)

b: oleic anhydride (or fatty acid anhydrides)

c: oleoyl chloride (or fatty acyl chlorides)

F.a. Esterification with Oleic Acid (or $C_{2-30}$ fatty acids): Crystalline sterols with >98.5% purity are treated with 1.0-1.5 moles of oleic acid (or $C_{2-30}$ fatty acids) at 120-300° C., preferably 180-250° C., while removing a by-product water in vacuum, preferably 0.01-10 torr, to make high purity sterol oleate or fatty esters (>98.5%).

F.b. Esterification with Oleic Anhydride (or $C_{2-30}$ fatty acid anhydrides): Crystalline sterols with >98.5% purity are treated with 0.5-0.75 moles of oleic anhydride (or $C_{2-30}$ fatty acid anhydrides) at 100-300° C., preferably 150-180° C. while forming a byproduct oleic acid (or fatty acids), which will be further reacted to complete the esterification at elevated temperatures such as 180-250° C. at 0.01-10 torr, to provide a high purity sterol oleate or fatty esters (>98.5%).

F.c. Esterification with Oleic Anhydride (or $C_{2-30}$ fatty acid anhydrides): Crystalline sterols with >98.5% purity are treated with 1.0-1.5 moles of oleyl chloride (or $C_{2-30}$ fatty acid chlorides) at 100-300° C., preferably 120-180° C., while removing a by-product HCl in vacuum, preferably 0.01-10 torr to provide a high purity sterol oleate or fatty esters (>98.5%).

What we claim is:

1. A process for recovering sterols from a crude source containing free sterols and their esters, which process comprises:
   (a) saponifying the crude source containing sterol esters to form free sterols;
   (b) extracting the free sterols of (a) with an organic solvent to yield an extract of a crude sterol concentrate containing from about 70 to 80% sterols by weight and fatty alcohols;
   (c) removing the fatty alcohols from the extract to an amount of 7% or less of fatty alcohols remaining in the extract;
   (d) crystallizing the extract of (c) with a solvent mixture of a C1-C10 hydrocarbon solvent present in an amount of about 60 to 99.9% by weight of the mixture, a C1-C10 alkanol present in an amount of about 0.1 to 20% by weight of the mixture, and water present in an amount of about 0.1 to 20% by weight of the mixture, to form crystallized sterols; and
   (e) recovering the crystallized sterols of (d) at a purity of at least 98%.

2. The process of claim 1 wherein the fatty alcohols are removed by distillation.

3. The process of claim 1 wherein the solvent mixture of (d) is about 80 to 98% by weight of the hydrocarbon solvent, about 1 to 10% by weight of the C1 to C10 alkanol, and about 1 to 10% by weight of water.

4. The process of claim 3 wherein the hydrocarbon solvent is comprised of a mixture of hexanes and heptanes.

5. The process of claim 3 wherein the C1 to C10 alkanol is methanol.

6. The process of claim 1 wherein the organic solvent of (b) is ethylenedichloride.

7. The process of claim 1 wherein the crystallizing is carried out at a temperature of from about 50 to 70° C.

8. The process of claim 1 which further comprises esterifying the crystallized sterols of (e) with an acylating agent to form sterol esters.

9. The process of claim 1 wherein the crystallized sterols are recovered at a yield of at least about 70% and a purity of at least about 98%.

10. The process of claim 1 wherein the crystallized sterols are recovered at a purity of greater than 98.5%.

11. The process of claim 9 wherein the crystallized sterols are esterified with an acylating agent to form sterol esters.

* * * * *